United States Patent [19]
Rosenblatt et al.

[11] 3,931,347
[45] Jan. 6, 1976

[54] PURIFICATION OF DINITROTOLUENE
[75] Inventors: David H. Rosenblatt, Baltimore; William H. Dennis, Jr., Braddock Heights, both of Md.
[73] Assignee: The United States of America as represented by the Secretary of the Army, Washington, D.C.
[22] Filed: Dec. 5, 1974
[21] Appl. No.: 529,873

[52] U.S. Cl. .............................................. 260/645
[51] Int. Cl.² ........................................ C07C 79/10
[58] Field of Search .................................... 260/645

[56] References Cited
FOREIGN PATENTS OR APPLICATIONS
459,169  2/1970  Japan ................................. 260/645

Primary Examiner—Leland A. Sebastian
Attorney, Agent, or Firm—Nathan Edelberg; Robert P. Gibson; A. Victor Erkkila

[57] ABSTRACT 2,4- and 2,6-Dinitrotoluenes are separated from mixtures thereof with small amounts of isomeric dinitrotoluene impurities by suspending the mixture in an aqueous solution containing a small amount of an alkali metal disulfide. The isomeric dinitrotoluene impurities are thereby converted to products soluble in the aqueous solution from which the 2,4- and 2,6-dinitrotoluenes can be recovered in excellent yield.

8 Claims, No Drawings

PURIFICATION OF DINITROTOLUENE

BACKGROUND OF THE INVENTION

Dinitrotoluene (DNT) is conventionally manufactured by nitrating toluene with a mixture of nitric and sulfuric acids. The crude dinitrotoluene thus obtained contains the desired 2,4- and 2,6-dinitrotoluene isomers along with small amounts, usually less than 5%, of isomeric dinitrotoluene impurities, notably the 2,3-, 2,5- and 3,4-dinitrotoluene isomers (so-called "meta" isomers). Dinitrotoluene is particularly valuable as an intermediate in the preparation of toluene diisocyanates employed in the manufacture of polyurethane foams and elastomers. In the preparation of products of this type, it is highly important to exclude the so-called "meta" isomers, since they contribute to the production of off-color, yellow polyurethane products. Dinitrotoluene is also valuable as an intermediate in the manufacture of 2,4,6-trinitroluene (TNT) employed as an explosive for military use. The TNT obtained by nitration of crude dinitrotoluene contains the desired 2,4,6-TNT isomer together with the undesired 2,4,5-, 2,3,4-, and 2,3,6-TNT isomers, which result from the nitration of the aforesaid "meta" isomers present in crude dinitrotoluene. At present TNT is purified by treatment with a hot solution of sodium sulfite (sellite) solution, which removes the undesired TNT isomers but results in a very concentrated and intensely reddish colored solution, whose disposal is costly and contributes to a serious pollution of streams into which it is discharged.

It is thus evident that the elimination of the so-called "meta" isomers in crude dinitrotoluene is highly desirable, since it would permit the production of superior polyurethane products and allow the manufacture of pure 2,4,6-TNT, thereby eliminating the need for sellite purification and attendant purification problems.

SUMMARY OF THE INVENTION

Accordingly, it is an object of the present invention to provide a process for the purification of crude dinitrotoluene. It is a further object of the invention to provide a process for separating 2,4- and 2,6-dinitrotoluenes from isomeric dinitrotoluene impurities with little loss of said 2,4- and 2,6-isomers. Other objects will become apparent from the following description of the invention.

In accordance with the process of the present invention 2,4- and 2,6-dinitrotoluenes are separated from mixtures thereof with small amounts of isomeric dinitrotoluene impurities by treatment of such mixtures with an aqueous solution containing a small amount of an alkali metal disulfide. The process of the present invention is advantageous in that it permits the purification of crude dinitrotoluene with the use of much smaller proportions of alkali metal disulfide and at lower temperatures than when sodium sulfite is employed according to the sellite purification process.

DETAILED DESCRIPTION OF THE INVENTION

The process of the present invention comprises mixing the impure dinitrotoluene with an aqueous solution containing a small amount of sodium or other alkali metal disulfide, preferably at temperatures between about 70° and 100°C., and then separating the purified DNT product from said aqueous treatment liquor. The present purification process is based on the discovery that the aqueous alkali metal disulfide reacts more rapidly with the so-called "meta" DNT isomers than with the desired 2,4- and 2,6-DNT isomers. It is believed that the "meta" DNT isomers undergo a nucleophilic reaction with the aqueous alkali metal disulfide, whereby the nitrogroups are displaced to form disulfide linkages. In the present process these "meta" isomers are converted to products, which are soluble in the aqueous treatment liquor and hence can be separated from the insoluble 2,4- and 2,6-DNT isomers.

The amount of alkali metal disulfide employed in the present process is sufficient to convert the aforesaid "meta" isomeric impurities to soluble products but insufficient to convert a substantial amount of the desired 2,4- and 2,6-DNT isomers. As illustrated in the example below, an amount of about 0.2 mol of aqueous alkali metal disulfide per mol of 2,4- and 2,6-DNT containing about 2 percent of "meta" isomeric impurities is sufficient to completely remove such "meta" isomers and permit a 96 percent recovery of pure 2,4- and 2,6-DNT isomers. When substantially larger proportions of alkali metal disulfide are employed, the undesired "meta" isomers are also completely removed but a lower yield of the 2,4- and 2,6-DNT isomers is obtained due to the reduction thereof apparently to nitrotoluidines. Such toluidines can build up and separate out and thereby contaminate the resulting 2,4- and 2,6-DNT product. However, such toluidines, if present, can be readily removed by extraction with aqueous hydrochloric or sulfuric acid; and they are automatically removed in the acid liquors when such purified DNT products containing toluidine impurities are nitrated to TNT in conventional manner. Since the alkali metal disulfide reacts more rapidly with the "meta" isomers than with the 2,4- and 2,6-DNT isomers, the degree of conversion and loss of the latter desired isomers can be controlled to some extent under such conditions by limiting the time of contact with the aqueous disulfide solution. When the impure dinitrotoluene contains larger proportions, e.g. 5 percent of said "meta" isomers, the amount of alkali metal disulfide can be correspondingly increased, e.g. to about 0.5 mol per mol of impure dinitrotoluene, to achieve complete removal of the "meta" isomers with little loss of the desired 2,4- and 2,6-DNT isomers. Obviously, if the ratio of alkali metal disulfide to impure dinitrotoluene or the contact time is excessively reduced, the removal of the undesired "meta" isomers will be less complete.

The aqueous alkali metal disulfide solution employed in the present process is preferably maintained at a pH of between about 9 and 11 by addition of a suitable base, e.g. sodium carbonate.

The present process is preferably carried out at temperatures between about 70°C. and about 100°C., since under these conditions the purification reaction is rapid and the dinitrotoluene is present as a liquid, which promotes intimate contact between the alkali metal disulfide liquor and the impure dinitrotoluene. The use of lower temperatures, e.g. room temperature, is also within the scope of the present invention but is less preferred, since the rate of purification is rather slow unless the dinitrotoluene is comminuted to a fine particle size. Temperatures above 100°C., are operative but less preferred, since they tend to produce lower yields of purified 2,4- and 2,6-DNT product.

The following example illustrates a specific embodiment of the method of carrying out the process of the present invention.

120 grams of crude dinitrotoluene were slurried with a solution of 12 grams of anhydrous sodium carbonate in 1 liter of distilled water at 75°C. To the slurry thus obtained was added with agitation a solution of sodium disulfide, obtained by dissolving 0.12 mol of powdered sulfur in 200 ml of water containing 0.12 mol of dissolved sodium sulfide ($NA_2S.9H_2O$). Five minutes after the addition was complete all of the 2,3- and 2,5-dinitrotoluene isomers had disappeared and 95 percent of the 3,4-isomer had been eliminated. Twenty minutes after the addition only the 2,4- and 2,6-dinitrotoluene isomers were present. The reaction mixture ws then cooled by addition of ice thereto and the solidified 2,4- and 2,6-dinitrotoluenes thus obtained were separated by filtration and dried. The purified 2,4- and 2,6-DNT mixture thus obtained weighed 115 grams, corresponding to a 96 percent yield based on the crude DNT starting material. Nitration of the product thus obtained with mixed nitric and sulfuric acids in conventional manner yielded pure 2,4,6-TNT directly.

The following table shows the progress of the reaction for removal of the isomeric dinitrotoluene impurities according to the foregoing example.

Molar ratio of $DNT:Na_2S_2$ = 5.5:1
Weight ratio of $DNT:Na_2S_2$ solution = 1:10
Concentration of $Na_2S_2$ = 0.10 molar
Temperature = 75°C.

| Reaction Time (minutes) = | | 0 | 1 | 2 | 5 | 10 | 15 | 20 |
|---|---|---|---|---|---|---|---|---|
| Analysis*: | 2,4-DNT | 83.62% | 80.98% | 80.95% | 81.22% | 78.49% | 79.54% | 80.48% |
| | 2,6-DNT | 14.44 | 17.98 | 18.33 | 18.72 | 21.48 | 20.45 | 19.52 |
| | 3.4-DNT | 1.25 | 0.65 | 0.39 | 0.06 | 0.02 | 0.01 | 0.00 |
| | 2,3-DNT | 0.55 | 0.38 | 0.32 | 0.00 | 0.00 | 0.00 | 0.00 |
| | 2,5-DNT | 0.12 | 0.00 | 0.00 | 0.00 | 0.00 | 0.00 | 0.00 |

*The analyses were performed by gas-chromatography as follows:

An aliquot of the reaction mixture was removed and extracted with $CH_2Cl_2$ (methylene chloride). The $CH_2Cl_2$ solution was washed successively with conc. $H_2SO_4$ to remove any toluidines present, and then with water to remove adhering acid. The washed $CH_2Cl_2$ solution was analyzed for DNT isomers by gas chromatography, wherein the isomers were separated isothermally using a 5' column glass U tube of ¼ I.D. containing 5% Carbowax 20M on 60/80 mesh Chromosorb W (AW) at 150°C. under atmospheric pressure. The order of elution was (from first to last) 2,6-DNT; 2,5-DNT; 2,4-DNT; 2,3-DNT; and 3,4-DNT. (Carbowax) 20M is a polyethyleneglycol having a molecular weight of 20,000, manufactured by the Union Carbide Corporation. Chromosorb W (AW) is an acid washed diatomaceous earth manufactured by the Johns-Manville Corporation).

While the example illustrates the purification of crude dinitrotoluene with aqueous sodium disulfide, other alkali metal disulfides, e.g. potassium disulfide, can be similarly employed with analogous results in the process of the present invention. The foregoing disclosure is merely illustrative of the principles of this invention and are not to be interpreted in a limiting sense. We wish it to be understood that we do not desire to be limited to the exact details of construction shown and described, because obvious modifications will occur to a person skilled in the art.

We claim:

1. A process for separating 2,4- and 2,6-dinitrotoluenes from isomeric dinitrotoluene impurities, which comprises suspending a mixture of 2,4- and 2,6-dinitrotoluenes containing a small amount of isomeric dinitrotoluene impurities, in an aqueous solution containing a small amount of an alkali metal disulfide which is sufficient to convert said isomeric dinitrotoluene impurities to water-soluble reaction products but insufficient to convert a substantial amount of said 2,4- and 2,6-dinitrotoluene isomers, and separating the insoluble 2,4- and 2,6-dinitrotoluenes from said aqueous mixture containing the water soluble reaction products of said isomeric dinitrotoluene impurities.

2. The process of claim 1, wherein the alkali metal disulfide is sodium disulfide.

3. The process of claim 2, wherein the mixture of 2,4- and 2,6-dinitrotoluenes contains less than 5 percent of isomeric dinitrotoluene impurities.

4. The process of claim 3, wherein the amount of sodium disulfide is not more than about 0.5 mol per mol of said mixture of 2,4- and 2,6-dinitrotoluenes.

5. The process of claim 3, wherein the aqueous slurry is maintained at a temperature above the melting point of the 2,4- and 2,6-dinitrotoluenes during the conversion step.

6. The process of claim 5, wherein the aqueous slurry is maintained at a temperature between about 70° and about 100°C. during the conversion step and thereafter cooled to solidify the 2,4- and 2,6-dinitrotoluenes prior to separation thereof from said slurry.

7. The process of claim 6, wherein the mixture of 2,4- and 2,6-dinitrotoluenes contains about 2 percent of isomeric dinitrotoluene impurities and the amount of sodium disulfide is between about 0.1 and about 0.3 mol per mol of said mixture of 2,4- and 2,6-dinitrotoluenes.

8. The process of claim 7, wherein the aqueous solution has a pH between about 9 and about 11.

* * * * *